United States Patent
Hulicsko et al.

[11] Patent Number: 5,967,999
[45] Date of Patent: Oct. 19, 1999

[54] BACK TRACTION DEVICE FOR A PATIENT

[76] Inventors: Leslie Hulicsko, P.O. Box 3344; John Nemeth, 1607 7th Ave., both of Regina, Canada

[21] Appl. No.: 08/490,230

[22] Filed: Jun. 14, 1995

[51] Int. Cl.⁶ ....................................................... A61F 5/00
[52] U.S. Cl. .............................................................. 602/32
[58] Field of Search .................... 602/32–40; 297/300.1, 297/300.4, 300.7, 301.1, 301.5, 303.4

[56] References Cited

U.S. PATENT DOCUMENTS

| | | |
|---|---|---|
| 951,560 | 3/1910 | Eaton . |
| 1,356,365 | 10/1920 | Hosmer . |
| 2,633,124 | 3/1953 | Yellin ........................................ 602/32 X |
| 2,633,125 | 3/1953 | Yellin . |
| 2,828,735 | 4/1958 | Thompson ................................. 602/32 |
| 2,984,238 | 5/1961 | Axtell et al. . |
| 3,299,886 | 1/1967 | Miken ................... 602/32 X |
| 3,960,145 | 6/1976 | Scarbrough . |
| 4,583,532 | 4/1986 | Jones . |
| 5,116,359 | 5/1992 | Moore . |

*Primary Examiner*—Richard J. Apley
*Assistant Examiner*—Kim M. Lee
*Attorney, Agent, or Firm*—Adrian D. Battison; Murray E. Thrift

[57] ABSTRACT

The present invention relates to a device and a method for applying traction to the back and neck of a patient. The traction device is inexpensive, relatively attractive and inconspicuous when mounted on a chair for use by the patient, and can be used with most household chairs.

12 Claims, 4 Drawing Sheets

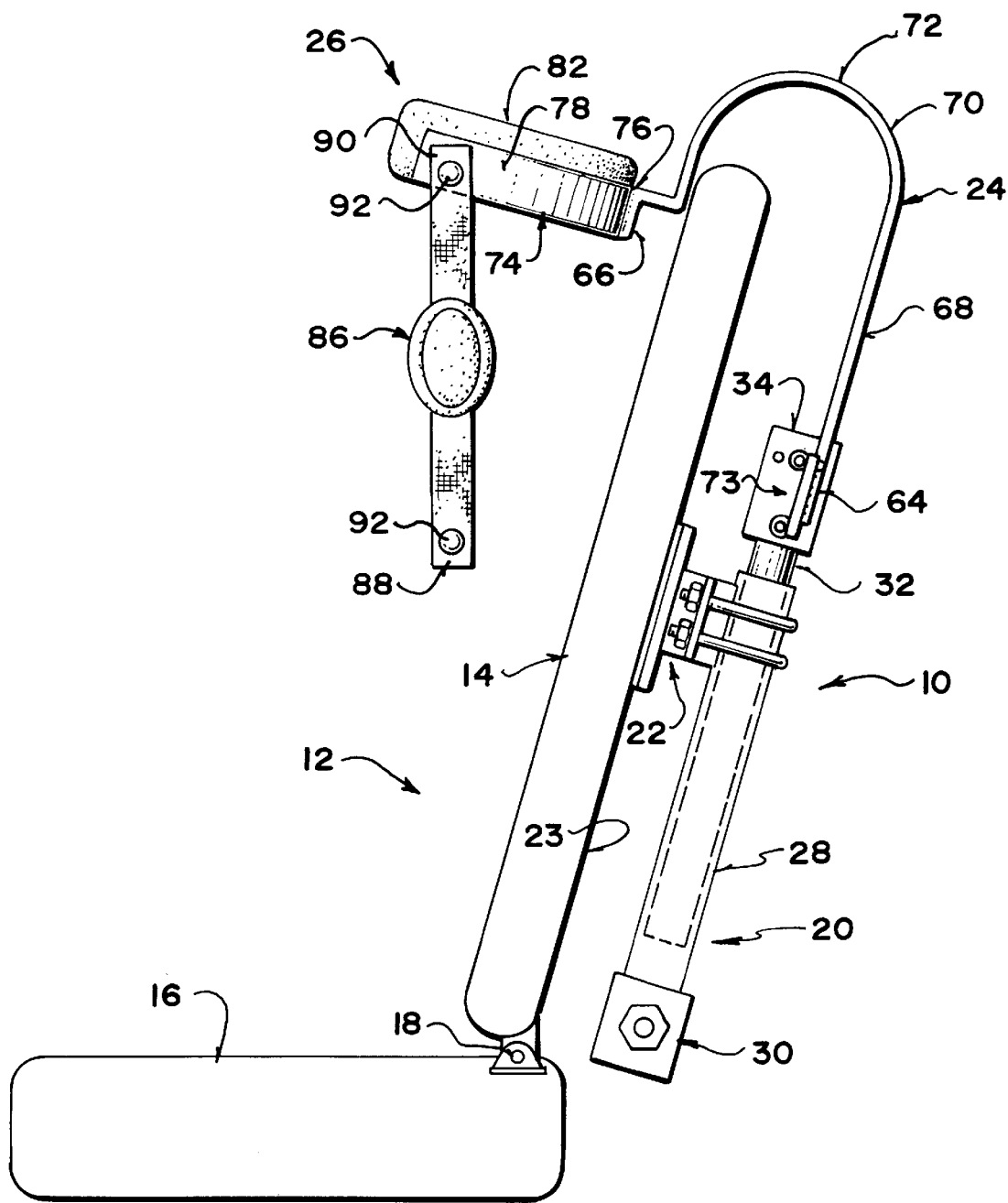
FIG. I

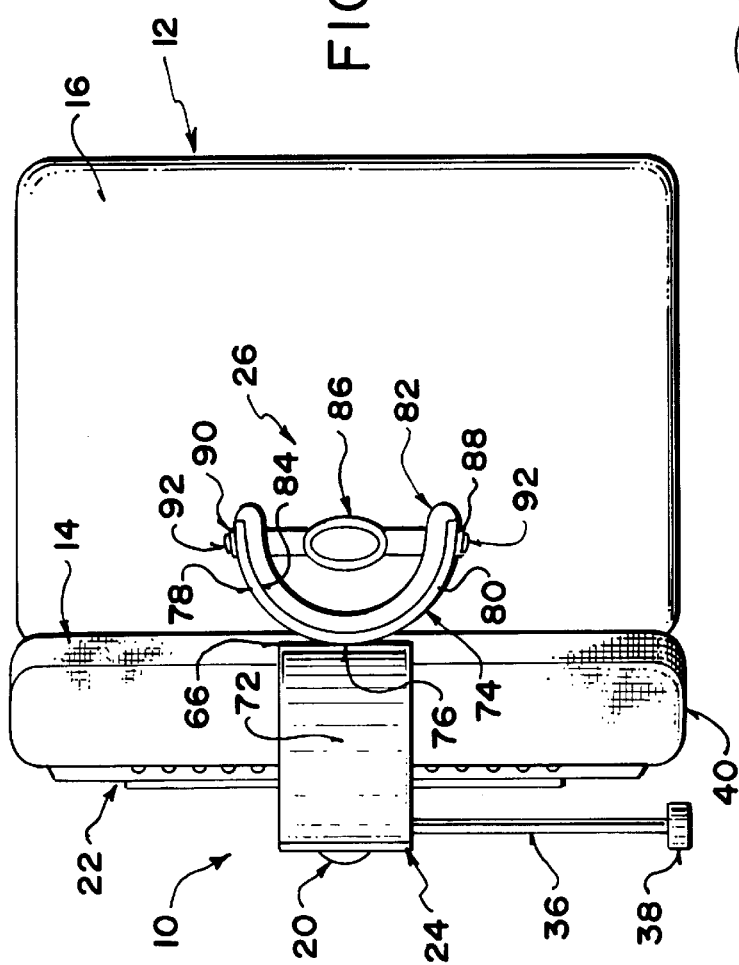
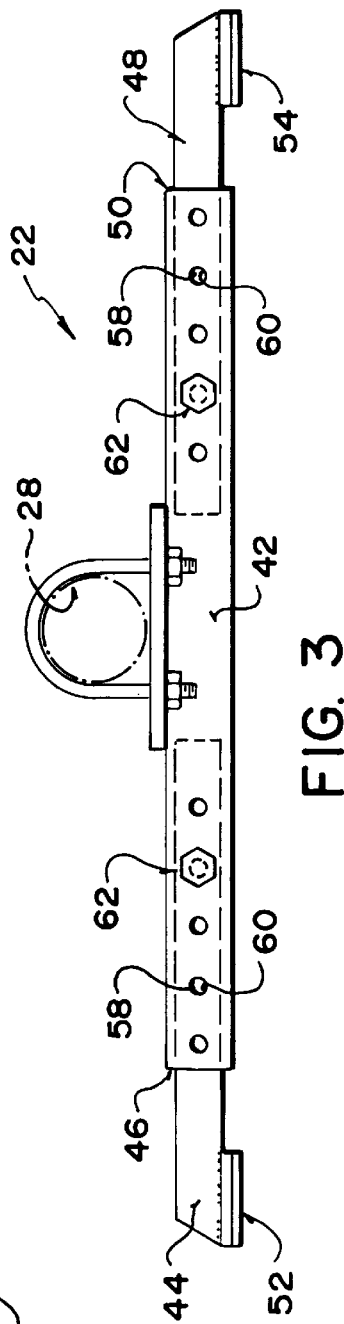

BACK TRACTION DEVICE FOR A PATIENT

FIELD OF THE INVENTION

The present invention relates to a device for applying traction to the back and neck of a patient.

BACKGROUND OF THE INVENTION

Traction devices are often employed by patients with back and/or neck problems of the type that can be positively affected by the application of a tensioning force to the back and/or neck.

These devices often comprise a chair and a traction apparatus fixed to the back of the chair. The apparatus usually includes a sling suspended from a cable for placing under the patients chin and around the back of the neck. The cable extends from a tensioning means upwards to an over hanging beam located above the head of the patient and then downwards to the sling. The tensioning means may or may not be adjustable by the patient when seated on the chair with the traction device in use.

These devices are simple in principal to use and therefore could be used by a patient with little or no supervision by a physician, but they are also currently expensive and often unnecessarily complex and therefore are primarily utilized at hospitals and clinics. Traveling to and from the hospital or clinic for treatment is often inconvenient or difficult for the patient and therefore presents a disincentive for the patient to continue with treatment over an extended period of time except in cases where the back or neck problem is serious.

A second problem of these devices is that they are usually gallows like in appearance, include a clinical looking chair, and are permanently fixed to the chair. This makes them unattractive for a patient who may wish to purchase one and have it for use at home, or to attach a traction device to an existing chair, thereby solving the problem of having to go to the hospital or clinic and making it easier to make beneficial use of traction on a more regular or continuous basis.

A traction device is needed therefore which is inexpensive, is relatively attractive and inconspicuous when mounted on a chair for use by the patient, and which can be used with most household chairs.

SUMMARY OF THE INVENTION

It is, one object of the present invention, therefore, to provide a traction device which is inexpensive, is relatively attractive and inconspicuous when mounted on a chair for use by the patient, and which can be used with most household chairs.

According to one aspect of the present invention there is provided a back traction device for a patient comprising: a chair for receiving the patient in a seated position having a seat bottom portion and a seat back; an elevation means arranged in a substantially vertical plane having an actuating means, a body, and a movable standard, the movable standard being arranged to extend above the body to a top end and to move relative to the body when the actuating means is actuated; attachment means for fixing the body of the elevation means to a rear surface of the seat back of the chair; a resilient member fixed at a bottom end to the top end of the movable standard of the elevation means extending therefrom upwards and forwards over the attachment means and the back of the chair to a free end above the seat bottom portion of the chair; and a head supporting member mounted at the free end of the resilient member and extending away from the resilient member and the back of the chair, said head supporting member being arranged for engaging under a chin of the patient.

Preferably the resilient member includes a first portion extending upwards from said elevation means to a curved portion, said curved portion curving upwards and forwards over the attachment means and the back of the chair to an apex of the curve, and then curving downwards to a free end in front of the back of the chair.

Preferably the resilient member is an elongate member which is resilient along its full length and pivotally fixed to the top end of the movable standard.

Preferably the elevation means is a screw jack or other elevation system which is adjustable upwards and downwards in small increments such as the linear actuators of the battery powered type which are currently becoming available at reasonable cost.

Preferably the attachment means comprise: a horizontal channel member fixed to the body of the elevation means; a first member positioned longitudinally and coaxially to the horizontal member, and being slidably connected towards one end of the horizontal member; a second member positioned longitudinally and coaxially to the horizontal member, and being slidably connected towards the other end of the horizontal member; attachment means located at one end of each of the respective first and second members for engagement with the back of the chair; and fixing means spaced along the horizontal channel member, the first member, and second member for fixing said respective first and second members in a plurality of positions relative to the horizontal member. The fixing means include: a plurality of holes spaced along the horizontal channel member; a plurality of holes spaced along each of the first and second members respectively, said plurality of holes in the first and second members being arranged for alignment with the plurality of holes on the horizontal channel member; and removable and reengageable fastening means for engagement through said aligned holes for fixing the first and second members relative to the horizontal channel member.

Preferably the head supporting member is a U-shaped member fixed at its base to the free end of the resilient member, and having arms extending forwards away from the resilient member and the back of the chair, said arms being sized and arranged to fit around the back of a head and neck of the patient. The arms of the U-shaped member include a pad arranged around an inner surface of the U-shaped member and a strap having two ends arranged such that each respective end of the strap is removably and reengageably connected to each respective arm for engagement under the chin of the patient thereby supporting the head.

According to a second aspect of the present invention there is provided a method for applying a back traction to a patient comprising: providing a chair having a generally upstanding back portion and a generally horizontal seat such that the back may recline about a horizontal axis of rotation adjacent a rear of the seat for adjustment of a recline angle; sitting the patient on the chair such that the hips of the patient are slightly forward of the back of the chair and the axis of rotation of the hips is forward of the axis of rotation of the back of the chair; providing a traction device mounted on the chair, and a head supporting member mounted on the traction device, said head supporting member extending outwards away from the back of the chair, and being arranged for engaging under a chin of the patient; placing the head of the patient in the head supporting member such that the head supporting member holds the head firmly at the chin; and increasing the tensioning force on the patient by increasing the recline angle of the back of the chair rearwardly relative to the seat.

Preferably the back of the chair is reclined by the patient applying a backwards pressure on the back of the chair while seated.

The chair is thus a conventional type chair readily available in the market and the traction device is simply attached to the rear surface of the chair back in a manner which cooperates with the chair to provide a simple adjustable tension on the patient's neck.

One embodiment of the invention will now be described in conjunction with the accompanying drawings in which:

BRIEF DESCRIPTION OF THE DRAWINGS

FIG. 1 is a side view of the traction device mounted on the back of a chair.

FIG. 2 is a top view of the traction device mounted on the back of a chair.

FIG. 3 is a top view of the attachment means of the traction device.

In the drawings like characters of reference indicate corresponding parts in the different figures.

DETAILED DESCRIPTION

Figure 4:
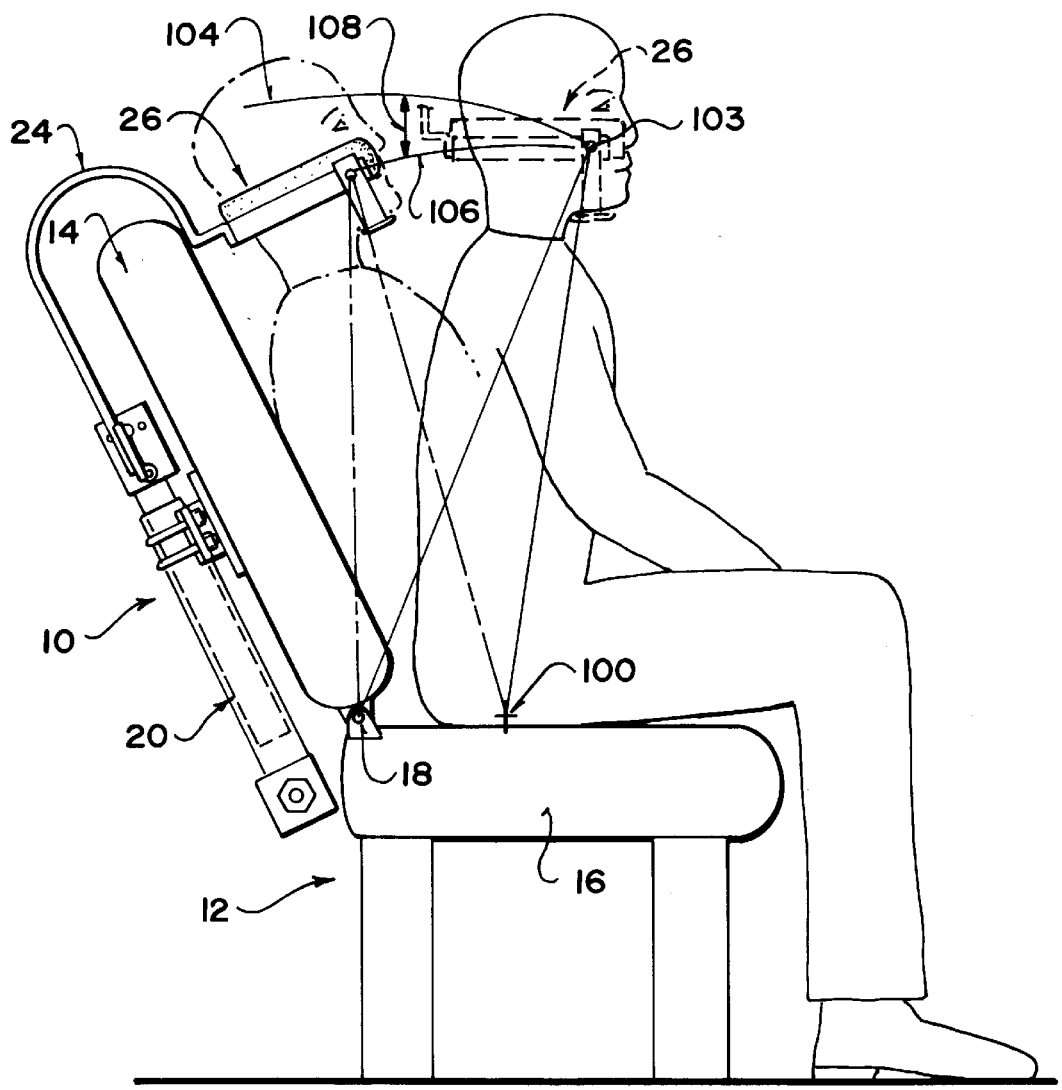
FIG. 4 is a side view of the traction device showing the method of increasing the tensioning force by reclining the chair back.

Referring to FIGS. 1 and 2 a preferred embodiment of the traction device is shown generally at 10 mounted on the back of a chair 12. The chair 12 includes a generally vertical seat back 14, a generally horizontal seat bottom 16, and a reclining mechanism 18 located at the junction of the seat back 14 and the seat bottom 16. The reclining mechanism 18 allows the seat back 14 to pivot about an axis of rotation lying in the horizontal plane. The traction device 10 can be used with a chair that does not have a reclining mechanism 18, but addition of a reclining mechanism 18 allows the patient to take advantage of the secondary means by which tension can be applied to the back and neck of the patient which is described in subsequent paragraphs.

The tension device 10 comprises elevation means 20 which provide a means of varying a tension to be applied to the patient, attachment means 22 which fix the device to the seat back 14 of the chair 12, a resilient member 24 connected to the elevation means 20, and a head supporting member 26 which is mounted on the resilient member 24 to communicate tensioning force to the patient.

The elevation means 20 is mounted behind the seat back 14 arranged in close to the seat back 14 so that the device is as inconspicuous as possible when viewed from the front or side of the chair 12. In the preferred embodiment a screw jack is employed as the elevation means 20. The screw jack 20 has a hollow cylindrical body 28 aligned in a substantially vertical plane with an actuating means 30 located at the bottom end of the body 28 and a movable standard 32 at the top end of the body 28. The actuating means 30 includes an arm 36 and a handle 38 which extend outwards past a side edge 40 of the chair 14. The arm 36 and handle 38 are positioned so that they can be turned by the patient while seated in the chair to adjust the vertical position of the movable standard 32 in small increments. The movable standard 32 is arranged to extend above the body 28 to a top end 34 and to move upwards and downwards in small increments relative to the body 28 when the actuating means 30 is actuated.

Referring to FIGS. 1 and 3 the attachment means 22 fix the body 28 of the screw jack 20 to a rear surface 23 of the seat back 14 of the chair 12. The attachment means 22 have a horizontal channel member 42 which is fixed to the body 28 of the screw jack 20. A first member 44 is positioned longitudinally and coaxially within the horizontal channel member 42 and towards one end 46 such that it may slide relative to the horizontal channel member 42. A second member 48 is positioned longitudinally and coaxially within the horizontal channel member 42 and towards the other end 50 such that it may slide relative to the horizontal channel member 42.

Fastening means 52 and 54 are located one at each respective end of the first and second members 44 and 48 for engagement with the seat back 14 of the chair 12. The fastening means preferably comprise a bolt plate connected to the chair 12 and the first and second members 44 and 48 by nut and bolt pairs, which allows the traction device to be attached to the chair and then removed when it is no longer needed. Any appropriate fastening means may be substituted for those described above.

A plurality of holes 58 are spaced along the horizontal channel member 42, and a plurality of holes 60 are spaced along each of the first and second members 44 and 48 respectively. The holes 60 in the first and second members 44 and 48 are arranged for alignment with the plurality of holes 58 on the horizontal channel member 42. Removable and reengageable fixing means 62, in this embodiment nuts and bolts, are engaged through the aligned holes 58 and 60 fixing the first and second members 44 and 48 in one of a plurality of positions relative to the horizontal member 42.

Referring to FIGS. 1 and 2, the resilient member 24 is fixed at a bottom end 64 to the top end 34 of the movable standard 32. The resilient member 24 is an elongate member or strap formed of a resilient or spring material such as spring steel which is rectangular in cross section and includes a first portion 68 that extends upwards from the top end 34 of the movable standard 32 to a curved portion 70. The curved portion 70 curves upwards and forwards over the attachment means 22 and the seat back 14 of the chair 12 to an apex of the curve 72, and then curves downwards to a free end 66. The free end 66 is positioned in front of the seat back 14 of the chair 12 and above the seat bottom 16 of the chair 12. This allows the device to mount the head supporting member 26 in a position to engage around the back of the head and neck of the patient while remaining as inconspicuous as possible when in place on the chair.

In one alternative embodiment the resilient member 24 can be pivotally fixed 73 by any appropriate means to the top end 34 of the movable standard 32. This allows the patient some movement of the head and neck in a horizontal plane while maintaining tension on the neck in the vertical plane.

Referring to FIGS. 1 and 2 the head supporting member 26 is mounted at the free end 66 of the resilient member 24 and extends away from the resilient member 24 and the seat back 14 of the chair 12. The head supporting member 26 has a U-shaped member 74 that is fixed at its base 76 to the free end 66 of the resilient member 24 and is arranged for engaging under a chin of the patient. The U-shaped member 74 has arms 78 and 80 extending forwards away from the resilient member 24 and the seat back 14 of the chair 12. The arms 78 and 80 are sized and arranged to fit around the back of the head and neck of the patient. A pad 82 is arranged around an inner surface 84 of the U-shaped member 74 to improve the comfort of the patient. A strap 86 having two ends 88 and 90 is arranged such that each respective end 88 and 90 of the strap 86 is removably and reengageably connected 92 by any appropriate removable and reengageable connection means to each respective arm 78 and 80. The strap 86 engages under the chin of the patient thereby supporting the head from below.

Referring to FIG. 4 the traction device in use can be employed using the following method. The chair 12 as described above has a seat back portion 14 and a seat bottom 16. The seat back 14 may recline about the horizontal axis of rotation 18 for adjustment of the recline angle.

After the traction device is installed on the back of the chair 12 the patient is seated on the chair 12 such that the hips of the patient are positioned slightly forward of the seat back 14 of the chair 12 and the axis of rotation of the hips 100 is therefore forward of the axis of rotation 18 of the seat back 14 of the chair 12.

The traction device 10 as described above having been mounted on the chair 12, with the head supporting member 26 extending outwards away from the seat back 14 of the chair 12, is positioned by raising or lowering the movable standard 32 via the actuating means 30 until the device is in place for engaging under the chin of the patient. The head and neck of the patient is placed in the head supporting member 26 with the strap 86 placed under the chin of the patient such that the head supporting member 26 holds the head firmly in place.

The tensioning force may be applied to the patient in one of two ways. The first being by operating the actuating means 30 on the screw jack 20 thereby raising the standard member 32 and therefore the head supporting member 26 which thereby applies a tension on the neck and back of the patient.

The second method of increasing the tensioning force is by increasing the recline angle of the seat back 14 of the chair 12 rearwardly relative to the seat bottom 16. This can be done by the patient applying a backwards pressure on the seat back 14 of the chair 12 while seated, or by another individual reclining the chair.

Reclining the chair increases the tension on the patient because the axis of rotation 18 of the seat back 14 and the axis of rotation of the hips 100 of the patient are spaced from one another. The neck of the patient and the head supporting member 26 which is fixed to the seat back 14 of the chair 12, start off coincident 103 but attempt to travel through diverging arcs 104 and 106 as they recline together. The tension will increase proportionally to the degree of divergence 108 of the two arcs 104 and 106. Therefore the head supporting member 26 applies an increasing tensioning force to the head as the seat is reclined and head supporting member 26 tries to draw the head of the patient "upwards". This method provides the patient with a simple means for varying the tension applied.

Figure 5:
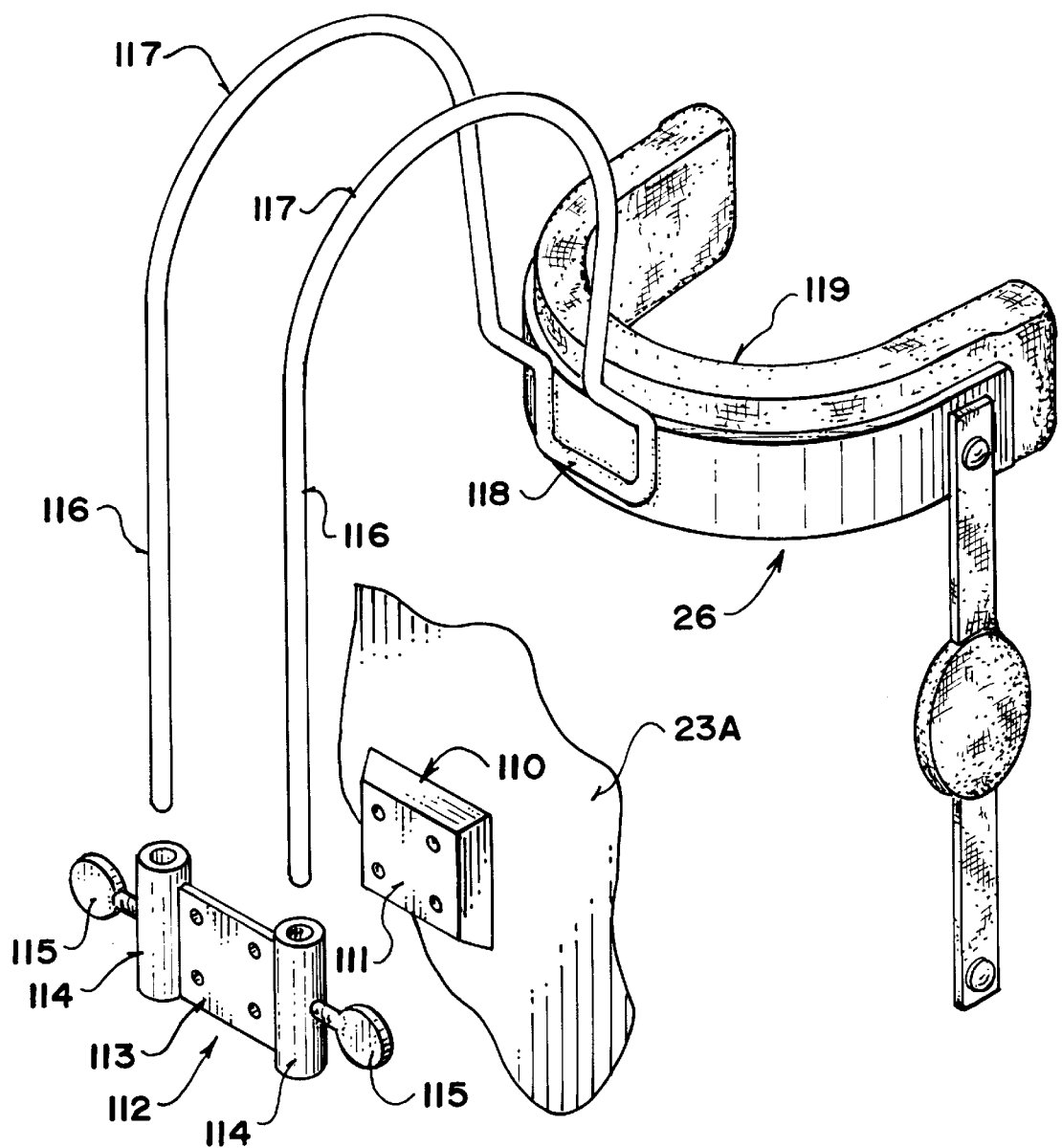
FIG. 5 is a schematic isometric view of a modified arrangement using a spring wire for providing the resilient member.

Turning now to FIG. 5 there is shown a modified arrangement in which the rear surface of a seat back 23A has attached to it a mounting block 100. The mounting block has support surface 101 generally parallel to the seat back 23A and supported away from the seat back by the mounting block itself. Onto the mounting block is attached a bracket 102 which includes a support plate 103 for clamping onto the surface 101 by suitable screw fasteners (not shown). The plate 103 carries on each side tubular sleeves 104 so that the tubular sleeves are supported on either side of the mounting block again lying in a plane generally parallel to the rear surface 23A. The tubular sleeves are also mutually parallel and include clamping screws 105 of a conventional nature for clamping the lower end of a wire 106 engaged into the respective sleeve 104. The wires 106 form the lower ends of a wire loop 107 which extends from the sleeves 104 upwardly and forwardly over a top edge of the seat back in the manner shown in FIG. 1. Thus instead of the resilient member being formed by a flat strap as shown in FIG. 1, the resilient member in FIG. 5 is defined by a wire loop of a spring steel providing the same resilient effect as the resilient member of FIG. 1. The forward end of the wire loop forms a horizontal bar portion 108 defining a base of the U-shape at the forward part of the wire loop 107. The horizontal bar 108 is attached to the U-shaped support member 26 for engaging the neck and rear of the head of the patient. The U-shaped support member is fastened to the horizontal bar for example by welding and carries a padded section 109 on its inside surface for engaging the head of the patient.

In the arrangement as shown, therefore, the device is much simpler in that the screw jack is omitted and the resilient member is directly attached to a mounting bracket on the rear face of the chair. An adjustment of the height of the support member 26 can be effected by manually adjusting the position of the wires 106 within the sleeves 104. In operation, therefore, the patient will set the height of the support member 26 at a required height relative to the position of his neck by a trial and error arrangement and then the patient can sit in the chair and effect the reclining action previously described. The wire loop and the support member 26 can be readily removed from the chair by releasing the wires 106 from the sleeves 104 so that the chair reverts to the appearance of a conventional chair for use by the patient at other times or by other persons.

The same bracket 102 can be used for attachment to the top of the screw jack in the arrangement of FIG. 1.

The screw jack can be of the type of battery powered linear actuator which is currently becoming available at reasonable cost. In the alternative the screw jack can be replaced by a hydraulic or pneumatic system actuated by a hand pump while the patient remains in the chair.

Since various modifications can be made in my invention as herein above described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. A method for applying a back traction to a patient comprising:

provoding a chair having a generally upstanding back portion and a generally horizontal seat the chair being arranged such that the back portion may recline about a first horizontal axis of rotation adjacent a rear of the seat for adjustment of a recline angle;

sitting the patient on the chair such that the hips of the patient on the seat are forward of the back portion of the chair such that the hips of the patient rotate about a second axis of rotation of the hips which is forward of the first axis of rotation of the back portion of the chair;

providing a traction device mounted on the back of the chair, and a head supporting member mounted on the traction device, said head supporting member extending forwards from the back of the chair to a position for engaging the head of the patient;

placing the head of the patient in the head supporting member;

generating a tensioning force in the back of the patient by pulling on the head supporting member in a direction to increase a distance of the head from the hips of the patient;

causing the hips of the patient to remain stationary in place on the seat;

and increasing the tensioning force on the patient by increasing the recline angle of the back of the chair rearwardly relative to the seat such that the distance from the hips of the patient to the head supporting member is increased by pivoting the head supporting member about the first axis while the head and back of the patient pivot relative to the hips of the patient about the second axis.

2. The method in accordance with claim 1 wherein the recline angle of the back of the chair is increased by the patient applying a backwards pressure on the back of the chair while seated.

3. The method in accordance with claim 1 wherein the traction device includes a movable standard, a mounting member attached to a rear surface of the chair back and a support member extending from an upper end of the movable standard over a top of the chair back to a free end at the head supporting member forwardly of the chair back.

4. The method in accordance with claim 3 including providing resilience between the head supporting member and the upper end of the movable standard by forming the support member along its full length from an elongate member of a resilient material so as to be resiliently deformable along its full length.

5. The method in accordance with claim 3 wherein the support member extends to the free end which is located behind the head of the patient and below a top of the head of the patient and wherein the head supporting member mounted at the free end of the support member extends forwardly from the free end of the support member, said head supporting member being arranged for engaging around the rear of the head of the patient and under the chin of the patient.

6. The method in accordance with claim 5 comprising forming the head supporting member as a U-shaped member having a base and two legs which is fixed at its base to the free end of the support member, and having the legs sized and arranged to fit around the back of the head and neck of the patient.

7. A method of providing back traction to a patient comprising:

providing a chair for receiving the patient in a seated position having a generally horizontal seat and a generally upstanding back portion and seating the patient in the chair;

providing an elevation means including a base body and a movable standard, the elevation means being actuable by the patient for movement of an upper end of the movable standard upwardly and downwardly;

fixing the base body of the elevation means to a rear surface of the back portion of the chair for movement of the movable standard relative to the back portion of the chair, the upper end of the movable standard being located rearwardly of the back portion;

providing a support member having a bottom end attached to the upper end of the movable standard of the elevation means and extending therefrom upwards and forwards over the back portion of the chair to a free end above the seat bottom portion of the chair, behind the head of the patient and below a top of the head of the patient;

and providing a head supporting member mounted at the free end of the support member and forwardly from the support member and the back of the chair, said head supporting member being arranged for engaging around the rear of the head of the patient and under the chin of the patient.

8. The method in accordance with claim 7 including providing resilience between the head supporting member and the upper end of the movable standard by forming the support member along its full length from an elongate member of a resilient material so as to be resiliently deformable along its full length.

9. The method in accordance with claim 7 wherein the support member includes a first portion extending upwards from said upper end of the movable standard to a curved portion, said curved portion curving upwards and forwards over the back portion of the chair to an upper apex, and then curving downwards to the free end in front of the back of the chair.

10. The method in accordance with claim 7 wherein the head supporting member is a U-shaped member having a base and two legs with the base fixed to the free end of the support member, and the legs extending forwards away from the back of the chair, said arms extending around the back of the head and neck of the patient.

11. The method in accordance with claim 10 including providing on each of the legs of the U-shaped member a pad arranged around an inner surface thereof.

12. A method of providing back traction to a patient comprising:

providing a chair for receiving the patient in a seated position having a generally horizontal seat and a generally upstanding back portion and seating the patient in the chair;

providing an elevation means including a base body and a movable standard, the elevation means being actuable by the patient for movement of an upper end of the movable standard upwardly and downwardly;

fixing the base body of the elevation means to a rear surface of the back portion of the chair for movement of the movable standard relative to the back portion of the chair, the upper end of the movable standard being located rearwardly of the back portion;

providing a support member having a bottom end attached to the upper end of the movable standard of the elevation means and extending therefrom upwards and forwards over the back portion of the chair to a free end above the seat bottom portion of the chair;

providing a head supporting member mounted at the free end of the resilient member for engaging around the rear of the head of the patient and under the chin of the patient;

and providing resilience between the head supporting member and the upper end of the movable standard by forming the support member along its full length from a single continuous elongate member of a resilient material so as to be resiliently deformable along its full length.

* * * * *